United States Patent [19]

Krauss et al.

[11] Patent Number: 5,470,302
[45] Date of Patent: Nov. 28, 1995

[54] MEDICAL APPARATUS HAVING AN ADJUSTABLE APPARATUS PART FOR APPLICATION TO THE BODY SURFACE OF A PATIENT

[75] Inventors: Guenther Krauss, Erlangen; Klaus Herrmann, Nuernberg, both of Germany

[73] Assignee: Siemens Aktiengesellschaft, Munich, Germany

[21] Appl. No.: 298,175

[22] Filed: Aug. 30, 1994

[30] Foreign Application Priority Data

Aug. 30, 1993 [DE] Germany ............... 43 29 167.8

[51] Int. Cl.⁶ ............................................. A61B 17/22
[52] U.S. Cl. ............... 601/2; 601/4; 128/660.03; 378/205
[58] Field of Search ............... 601/2, 3, 4; 128/660.03, 128/653.1; 5/601; 378/205

[56] References Cited

U.S. PATENT DOCUMENTS

| | | | |
|---|---|---|---|
| 4,674,505 | 6/1987 | Pauli et al. . | |
| 4,697,588 | 10/1987 | Reichenberger . | |
| 4,796,613 | 1/1989 | Heumann et al. . | |
| 4,811,725 | 3/1989 | Grasser | 601/4 |
| 4,877,017 | 10/1989 | Hahn et al. | 601/4 |
| 4,971,039 | 11/1990 | Noske et al. | 601/4 |
| 5,036,836 | 8/1991 | Terai et al. | 601/4 |
| 5,044,354 | 9/1991 | Goldhorn et al. | 601/4 |
| 5,078,124 | 1/1992 | Viebach et al. | 601/4 |
| 5,081,984 | 1/1992 | Wess et al. . | |
| 5,090,401 | 2/1992 | Schweiker | 601/4 |
| 5,199,420 | 4/1993 | Artmeier | 601/4 |

FOREIGN PATENT DOCUMENTS

| | | |
|---|---|---|
| 0373967 | 6/1990 | European Pat. Off. . |
| 1238308 | 4/1967 | Germany . |

*Primary Examiner*—Krista M. Zele
*Attorney, Agent, or Firm*—Hill, Steadman & Simpson

[57] ABSTRACT

A medical apparatus has an apparatus part which is provided for application against the body surface of a patient, and a patient support mechanism and a system for adjusting the apparatus part and the patient support mechanism relative to each other. The system simultaneously adjusts the apparatus part at a first adjustment speed in a first direction and the patient support mechanism at a second adjustment speed in a second direction, with the first and second adjustment speeds having a fixed constant relationship, so that the apparatus part and the patient support mechanism are caused to execute a motion in a third direction relative to each other. The third direction can be selected to compensate for dislocations of the body of the patient which are anticipated upon the application of the apparatus part to the patient's body surface, so that the patient remains as stationary as possible.

7 Claims, 4 Drawing Sheets

MEDICAL APPARATUS HAVING AN ADJUSTABLE APPARATUS PART FOR APPLICATION TO THE BODY SURFACE OF A PATIENT

BACKGROUND OF THE INVENTION

1. Field of the Invention

The present invention is directed to a medical apparatus of the type having an apparatus part provided for application to the body surface of a patient, a patient support mechanism, and means for adjusting the apparatus part and the patient support mechanism relative to each other.

2. Description of the Prior Art

In medical apparatuses of the type generally described above, adjustment of the apparatus part and of the patient support mechanism can ensue relative to each other by adjusting the position only of the apparatus part or adjusting the position only of the support mechanism, or by adjusting the positions of both the support mechanism and the apparatus part.

In an apparatus of this type, the means for adjusting the apparatus part and the patient support mechanism relative to each other are provided for, among other things, permitting the application of the apparatus part to the body surface of the patient for therapeutic or diagnostic purposes. The apparatus may therefore be a therapy apparatus wherein the apparatus part is a source of acoustic waves, which is applied to the body surface of the patient for acoustic coupling by adjusting the source and the patient support mechanism relative to each other before implementation of a treatment. The source is in turn decoupled from the body surface of the patient after completion of the treatment. In an apparatus of this type, the source of acoustic waves is usually applied to the body surface of the patient after the patient has been positioned (aligned) with a locating system, such an x-ray system or an ultrasound system, so that the region to be treated is situated in a position which coincides with the therapeutic region of action of the acoustic waves generated by the source. When the source is then subsequently applied to the body surface of the patient, there is the risk that the region to be treated may become dislocated as a consequence of the forces which arise as the source is coupled to the body of the patient. Experience has shown that such dislocations increase in proportion to the extent that the direction of application of the source to the patient deviates from a direction which is normal to the region of the body surface to which the source is applied.

SUMMARY OF THE INVENTION

It is an object of the present invention to provide a medical apparatus of the type generally described at the outset which can be operated to reduce the dislocation of the body of the patient which occurs upon the application of the therapeutic or diagnostic apparatus part to the patient.

The above object is achieved in accordance with the principles of the present invention in a medical apparatus having an apparatus part provided for application against the body surface of a patient, a patient support mechanism, and means for adjusting the apparatus part and the patient support mechanism relative to each other synchronously in first and second directions, so that the apparatus part and the patient support mechanism execute a motion in a third direction relative to each other. It is thus possible to select the direction of the relative motion, i.e., the third direction, so as to keep dislocations of the body of the patient upon the application of the apparatus part thereto to a minimum.

In a preferred embodiment of the invention the therapeutic or diagnostic apparatus part is adjustable at least in the first or second direction before the relative motion of the apparatus part and the patient support mechanism takes place in the third direction, the diagnostic or therapeutic apparatus part being adjustable to such an extent that it assumes a defined position at the completion of the adjustment of the apparatus part and of the patient support mechanism relative to each other in the third direction. This is particularly important when it is necessary that the therapeutic or diagnostic apparatus part assume a defined position relative to another apparatus component at the end of the relative motion in the third direction.

In one version of the invention, the apparatus part which is intended for application against the body surface of the patient can be adjusted by the aforementioned means for adjusting from a standby position into a working position, and vice versa. It is thus not necessary to effect the entire adjustment on the basis of a relative motion in the third direction. Instead, the apparatus part intended for application to the patient can be adjusted from the standby position into the working position via an intermediate position, and vice versa, with the adjustment from the intermediate position into the working position and vice versa ensuing on the basis of the aforementioned relative motion in the third direction. The synchronous actuation of the means for adjusting therefore must ensue only during the adjustment from the intermediate position into the working position, and vice versa.

DESCRIPTION OF THE PREFERRED EMBODIMENTS

Figure 1:
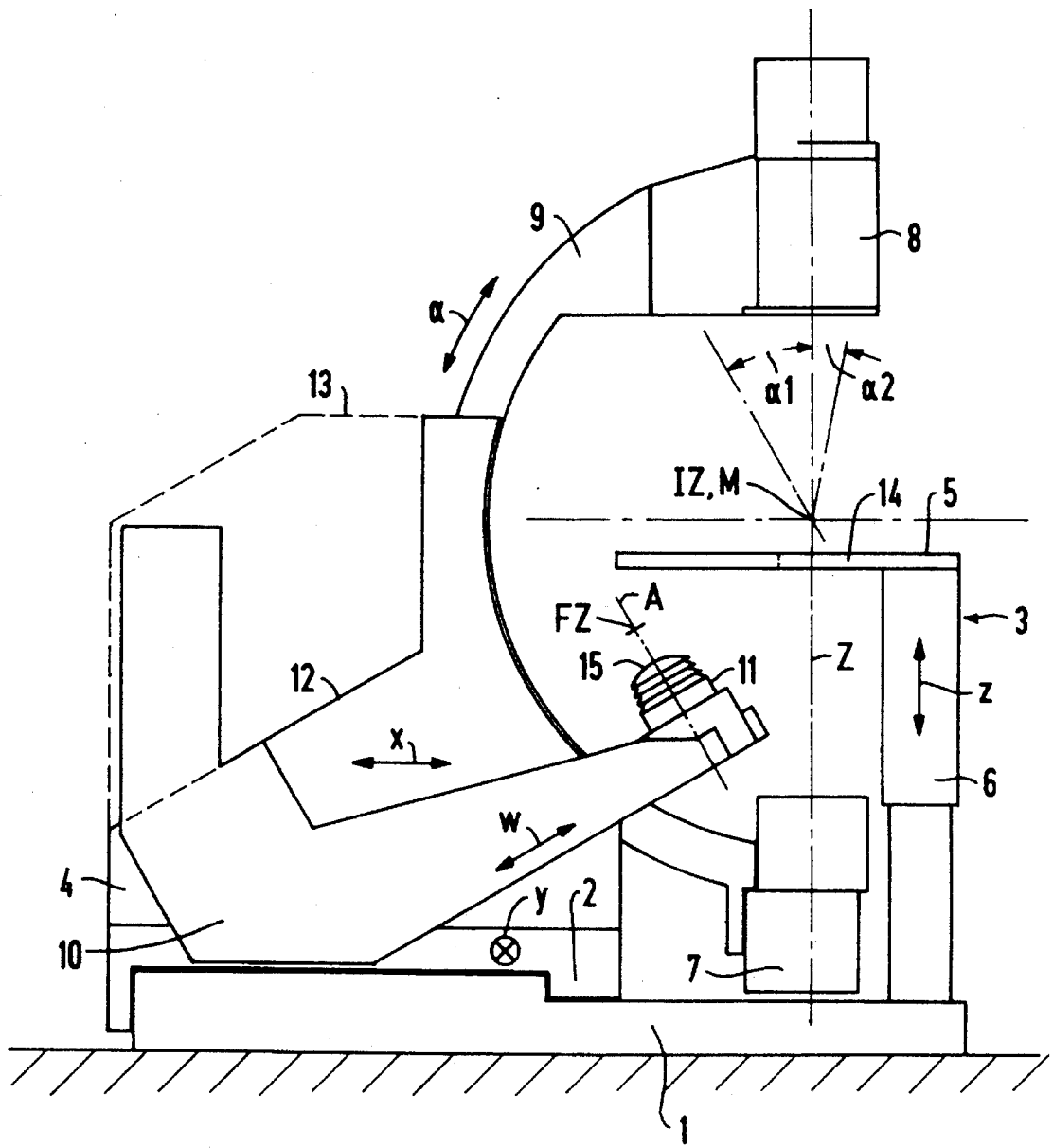
FIG. 1 is a schematic illustration of an apparatus constructed in accordance with the principles of the present invention, in the embodiment of an apparatus for therapy treatment with acoustic waves, in a first operating condition, shown in a front view.
Figure 2:
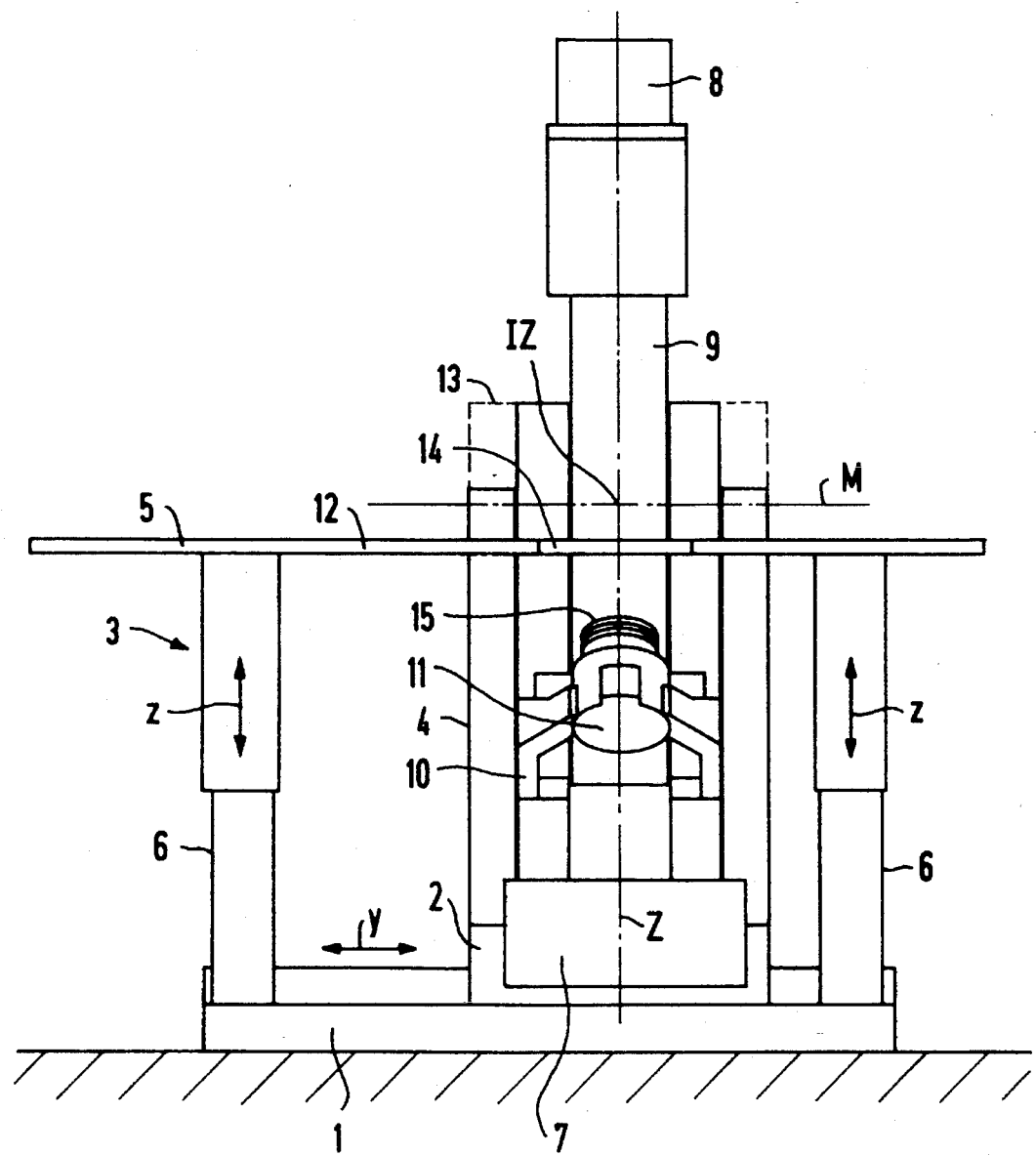
FIG. 2 is a schematic illustration of the apparatus of FIG. 1, in the first operating condition, shown in a side view.

The embodiment of the inventive apparatus shown in FIG. 1 includes a pedestal 1 on which a carriage 2 is adjustable in the y-direction proceeding parallel to the longitudinal axis of a patient support table 3. A carrier part 4 is attached to the carriage 2 so as to be longitudinally displaceable in the x-direction, transversely relative to the y-direction, and thus also transversely relative to the longitudinal axis of the patient support table 3. The support plate 5 of the patient support table 3 is height-adjustable in the z-direction. To this end, the patient support table 3 has two telescoping columns 6 disposed spaced from each other in the longitudinal direction of the patient support table 3.

An x-ray locating system is attached to the carrier part 4. The x-ray locating system includes an x-ray radiator 7 and an x-ray image intensifier 8, which are mounted at the ends of a C-arm 9 so as to be disposed opposite each other.

The C-arm 9 is connected to the carrier part 4 in a known manner, not shown in detail, so that it can be adjusted along its circumference in the direction of the curved double arrow α around its center axis M. It is thus possible to transirradiate a patient lying on the patient support table 3 from different directions. In the figures, the x-ray locating system is shown in a middle position, wherein a central ray Z of the x-ray locating system proceeds vertically. The respective directions of the central ray Z for two different transirradiation directions are indicated with dashed lines in FIG. 1, respectively describing angles $\alpha_1$ and $\alpha_2$ relative to the vertical.

An apparatus part adapted for application against the body surface of a patient to be treated, which in the embodiment of the drawings is a therapy unit in the form of a source 11 of focused acoustic waves, is also attached to the carrier part 4 with a mount 10. By adjusting the mount 10 in a first direction w along a guideway 12 located beneath a cover 13 indicated with dashed lines, the source 11 can be adjusted from a standby position shown in FIG. 1 relative to the carrier part 4 into a working position shown in FIG. 4. In the working position of FIG. 4, the source 11 projects through an opening 14 in the support plate 5. In this position, the focus zone FZ of the acoustic waves emitted by the source 11 is located in an isocenter IZ which corresponds to the intersection of the central axis M of the C-arm 9 with the central ray Z of the x-ray locating system. The focus zone FZ lies on the acoustic axis A of the source 11. The source 11 has a flexible application bellows 15 with which it presses against the body surface of the patient for acoustic coupling during the treatment. The source 11 can be adjusted in a second direction by adjusting the carrier part 4 in the x-direction. Means are thus provided for adjusting the source 11 relative to the patient support table 3 in first and second directions.

The source 11, for example, may be an electromagnetic pressure pulse source which emits focused shockwaves, as disclosed in greater detail in U.S. Pat. No. 4,674,505.

Adjustment of the carriage 2 in the y-direction, the carrier part 4 in x-direction, the standby plate 5 in the z-direction, the mount 10 in the w-direction, and the C-arm 9 in the α direction respectively ensues by motor drive, preferably electric motors. Suitable gearings may be employed as required.

In addition to the possibility of driving the respective motors respectively allocated to the different motion directions individually in forward or reverse, there is also the possibility, for the reasons described above, of synchronously driving the motors allocated to the x-direction and to the w-direction, in forward or reverse, so that a motion of the source 11 and of the support plate 5 relative to each other arises which proceeds in a third direction, namely in the direction of the acoustic axis A of the source 11. This enables an application of the source 11 against the body surface of the patient, or in an opposite direction to decouple the source 11 from the patient. Because, in the case of illustrated exemplary embodiment, this relative motion is realized only by adjusting the source 11, the source 11 is adjusted along its acoustic axis A given the synchronous drive of the motors responsible for the x-direction and w-direction adjustments.

Figure 3:
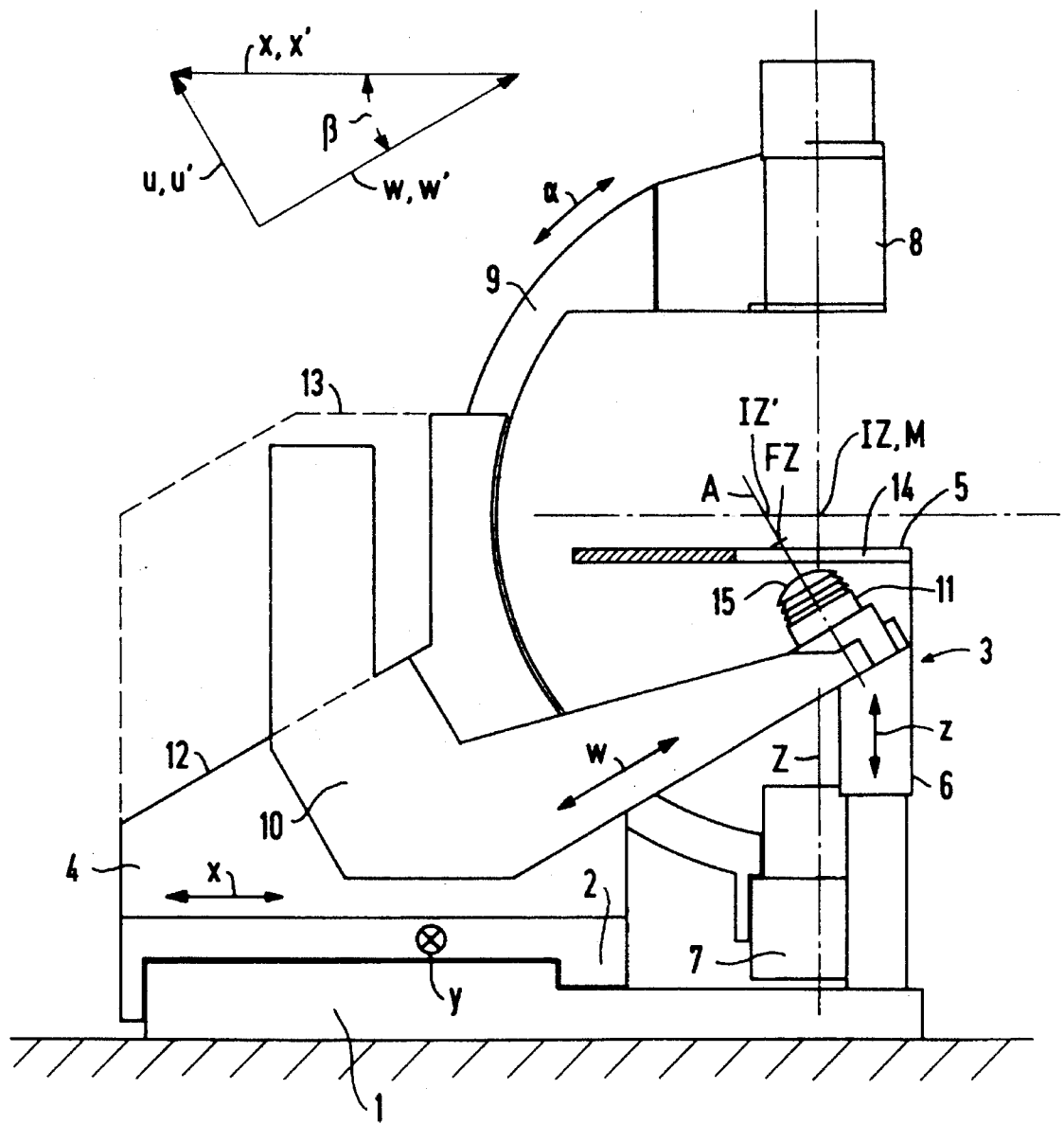
FIG. 3 is a schematic illustration of the apparatus of FIG. 1 in a second operating condition, partly in section of the FIG. 1, shown in a side view.

Because the acoustic axis A of the source 11 in the illustrated embodiment proceeds at a right angle relative to the w-direction, and the w-direction intersects the x-direction at an angle β (see FIG. 3), the drive of the motors responsible for the x-direction and w-direction adjustments must ensue in order to achieve the desired relative motion—the direction thereof being referenced u below, so that the relationship $$\frac{w'}{x'} = \cos\beta$$

applies for the adjustment speed x' in the x-direction and the adjustment speed w' in the w-direction, as referenced in FIG. 3. Correspondingly, $$\frac{w}{x} = \cos\beta$$

is valid for the distances traversed in the x-direction and the w-direction—referenced x and w in FIG. 3—for every point in time of the relative motion.

The relationships $$u' = \sqrt{x'^2 + w'^2}$$

and $$u' = \sqrt{x^2 + w^2}$$

are valid for the adjustment speed u' in the u-direction, and for the distance u traversed in the u-direction at a given point in time of the relative motion.

For implementing a treatment, the patient is placed on the support plate 5 so that the region of the patient to be treated is located above the opening 14 in the support plate 5. When the source 11 is in its standby position, the region to be treated is brought into the isocenter IZ by adjustment in the x-, y- and z-directions by transirradiating the patient with the x-ray locating system from the two directions $\alpha_1$ and $\alpha_2$. The position of the isocenter IZ is identified in a known manner by means of a mark mixed in the x-ray image which is displayed on a television monitor.

After the region to be treated is located in the isocenter IZ, the source 11 can be adjusted from its standby position into its working position. This occurs by first adjusting the source 11 in the w-direction into an intermediate position shown in FIG. 3, proceeding from which the source 11 is brought into its working position, shown in FIG. 4, by an obliquely upwardly directed motion in u-direction. The focus zone FZ is located in the isocenter IZ in this working position of the source 11.

Because the isocenter IZ is also displaced upon adjustment in the u-direction as a consequence of the fact that the adjustment in the u-direction is produced by a combined adjustment in the x-direction and in the w-direction, the carrier part 4 is displaced in the x-direction toward the patient support table 3 in order to set the intermediate position shown in FIG. 3. This displacement represents the amount by which the carrier part 4 must in turn be adjusted away from the patient support table 3, given the motion of the source 11 in the u-direction, in order to bring the focus zone FZ into coincidence with the isocenter IZ. The position that the isocenter IZ assumes when the source 11 has reached its working position is referenced IZ' in FIG. 3.

Figure 4:
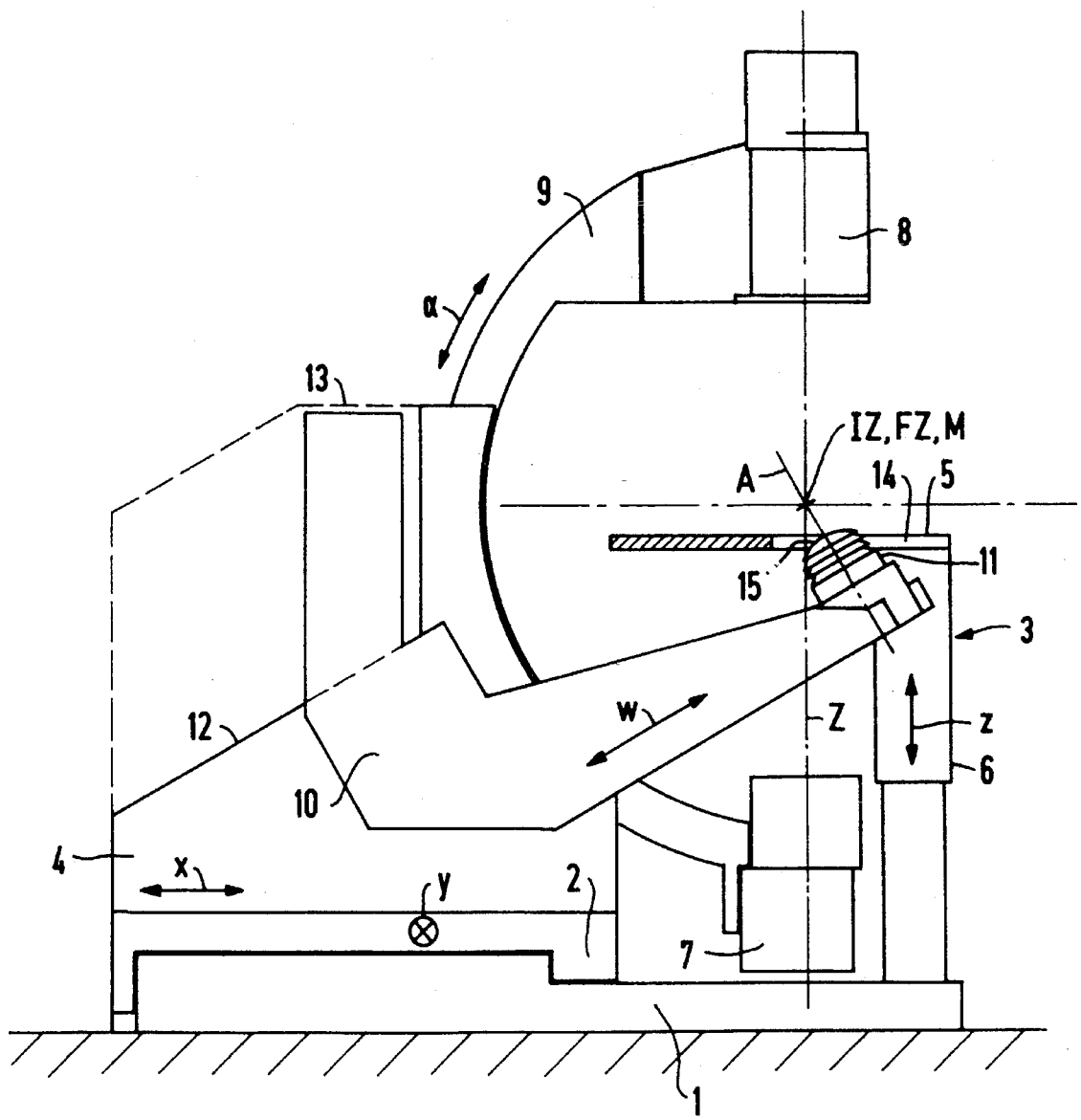
FIG. 4 is a schematic illustration of the apparatus of FIG. 1 in a third operating condition, partly in section.

Proceeding from the intermediate position shown in FIG. 3, the source 11 is adjusted obliquely upwardly in the u-direction into its working position shown in FIG. 4 by a synchronous drive of the motors which are responsible for the x-direction and the y-direction adjustments in the above-described manner.

The treatment of the patient can now ensue. If necessary, a fine locating readjustment can occur before the treatment, with any slight dislocations of the patient which may possibly have occurred being corrected.

Following the treatment, the source 11 is decoupled from the body surface of the patient by first adjusting the source 11 in the u-direction obliquely downwardly into the intermediated position of FIG. 3. Proceeding from this intermediate position, the source 11 is in turn moved in reverse in the w-direction into the standby position shown in FIG. 1. Simultaneously, the carrier part 4 is adjusted away from the patient support table 3 in the x-direction by that amount by which it was displaced in the direction toward the patient support table 3 in the x-direction during the adjustment of the source 11 from the working position into the intermediate position.

The invention has been described above with reference to a therapy apparatus for treatment with acoustic waves, particularly suitable for lithotripsy. The inventive concept disclosed herein, however, can be employed in any type of therapy or diagnostic apparatus which includes an apparatus part to be applied to the body surface of a patient.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical apparatus comprising:

an apparatus part adapted for application against the body surface of a patient; patient support means adapted for supporting said patient; and means for adjusting said apparatus part at a first adjustment speed in a first direction and for simultaneously adjusting said patient support means at a second adjustment speed in a second direction with said first and second adjustment speeds in said first and second directions having a fixed constant relationship for causing said apparatus part and said patient support means to execute a motion relative to each other exclusively in a third direction for minimizing displacement of said patient upon the application of said apparatus part to said body surface of said patient.

2. A medical apparatus as claimed in claim 1 wherein said means for adjusting comprises means for adjusting said apparatus part in at least one of said first and second directions, before said apparatus part and said patient support means executes said relative motion in said third direction, by an amount for causing said apparatus part to assume a defined position upon completion of adjustment of said apparatus part and said patient support means relative to each other in said third direction.

3. A medical apparatus as claimed in claim 1 wherein said means for adjusting comprises means for adjusting said apparatus part from a standby position wherein said apparatus part is not applied to said body surface of said patient into a working position wherein said apparatus part is applied to the body surface of said patient, and from said working position to said standby position.

4. A medical apparatus as claimed in claim 3 wherein said means for adjusting comprises means for adjusting said apparatus part from said standby position into said working position via an intermediate position, and for adjusting said apparatus part from said working position into said standby position via said intermediate position.

5. A medical apparatus as claimed in claim 4 wherein said means for adjusting comprises means for adjusting said apparatus part from said intermediate position by said relative motion in said third direction, and for adjusting said apparatus part from said working position to said intermediate position by said relative motion in said third direction.

6. A medical apparatus as claimed in claim 1 wherein said apparatus part comprises a source of therapeutic acoustic waves.

7. A medical apparatus as claimed in claim 6 wherein said source of acoustic waves has an acoustic axis, and wherein said means for adjusting comprises means for adjusting said source of acoustic waves and said patient support means in said first and second directions for causing said source of acoustic waves and said patient support means to execute a motion relative to each other in a third direction coinciding with said acoustic axis.

* * * * *